United States Patent [19]

Trautwein

[11] Patent Number: 5,739,436

[45] Date of Patent: Apr. 14, 1998

[54] METHODS AND APPARATUS FOR MEASURING DOUBLE-INTERFACE SHEAR IN GEOSYNTHETICS AND GEOMATERIALS

[76] Inventor: Stephen J. Trautwein, P.O. Box 3149, Houston, Tex. 77231

[21] Appl. No.: 679,935

[22] Filed: Jul. 15, 1996

Related U.S. Application Data

[63] Continuation of Ser. No. 390,760, Feb. 17, 1995, abandoned.

[51] Int. Cl.$^6$ .................................................. G01N 3/24
[52] U.S. Cl. ................................................ 73/841; 73/846
[58] Field of Search ............................ 73/841, 842, 846, 73/818, 819

[56] References Cited

U.S. PATENT DOCUMENTS

| | | |
|---|---|---|
| 2,656,718 | 10/1953 | Dames et al. . |
| 3,086,391 | 4/1963 | Schmitt-Thomas et al. . |
| 3,673,861 | 7/1972 | Handy . |
| 3,745,051 | 7/1973 | Griffin et al. . |
| 4,075,855 | 2/1978 | Handy et al. . |
| 4,539,851 | 9/1985 | Lutenegger . |
| 4,825,700 | 5/1989 | Vardoulakis et al. . |
| 4,854,175 | 8/1989 | Budhu . |
| 5,063,785 | 11/1991 | Labuz et al. . |
| 5,319,958 | 6/1994 | Date et al. . |

FOREIGN PATENT DOCUMENTS

| | | | |
|---|---|---|---|
| 2723087 | 11/1978 | Germany . | |
| 0192240 | 9/1985 | Japan . | |
| 63284468A | 11/1988 | Japan .......................... | 73/841 |
| 1157386 A | 9/1982 | U.S.S.R. . | |
| 1411629 A1 | 8/1986 | U.S.S.R. . | |
| 1534371 A2 | 4/1988 | U.S.S.R. . | |
| 1609853A | 11/1990 | U.S.S.R. ................... | 73/841 |
| 2151798 | 7/1985 | United Kingdom ............. | 73/841 |

OTHER PUBLICATIONS

ASTM D 3080, "Standard Test Method for Direct Shear Test of Soils Under Consolidated Drained Conditions", American Society for Testing & Materials, (1990), Philadelphia, PA.

ASTM D 5321, "Standard Test Method for Determining the Coefficient of Soil & Geosynthetic or Geosynthetic & Geosynthetic Friction by the Direct Shear Method", (1992), Am. Soc. for Testing Mat'l., Phil.

Byrne, R.J., et al., "Cause & Mechanism of Failure, Kettleman Hills Landfill B–19, Unit IA", (1992), Proc. ASCE Spec. Conf. on Performance & Stability of Slopes & Embankments–II, vol. 2, pp. 1188–1215.

Geosyntec "Draft Final Report, Landfill Unit B–19, Phase IA Investigation, Kettleman Hills Facilities., Kettleman City, CA", Report Prepared for Chemical Waste Mgmt, Inc. by Geosyntec Cons., (1992), Atlanta, GA.

Gilbert, R.B., et al., "Strain-Softening Behavior of Wasted Containment System Interfaces", (1994; paper in progress) published in Geosynthetics International 3:181–201, 1996.

Seed, R.B., et al., "Slope Stability Failure Investigation: Unit B–19, Phase I–A, Kettleman Hills, CA.", (1988), Research Report No. UCB/GT/88–01, Univ. of CA, Berkeley, CA.

Shan, H.Y., "Stability of Final Covers Placed on Slopes Containing Geosynthetic Clay Liners", (1993), Ph.D. Dissertation, University of Texas, Austin, Texas.

Stark, T.D., et al., "Landfill Liner Interface Strengths from Torsional Ring Shear Tests", (1994), J. of Geotech. Engrg. ASCE, 120(3), pp. 286–293.

Olson, R.E., "Types of Laboratory Apparatus for Shear Testing of Soils", (1975), University of Texas.

U.S. Army Corps of Engineers, "Torsion Shear Apparatus and Testing Procedures", (1952), Vicksburg, MS, pp. 1–76.

*Primary Examiner*—Richard Chilcot
*Assistant Examiner*—Max H. Noori
*Attorney, Agent, or Firm*—Fish & Richardson P.C.

[57] ABSTRACT

The present invention generally provides a double-interface shear device for measurement of interface strength between geosynthetics and geomaterials. The device provides for the convenient application of normal loads, for the measurement of interface strength prior to and following deformation along the interface, and for the measurement of volume changes of the specimen normal to the interface. In addition, the invention provides methods of measuring shear strength of the interface between geoengineering materials.

16 Claims, 17 Drawing Sheets

METHODS AND APPARATUS FOR MEASURING DOUBLE-INTERFACE SHEAR IN GEOSYNTHETICS AND GEOMATERIALS

This is a continuation of application Ser. No. 08/390,760, filed Feb. 17, 1995, now abandoned.

BACKGROUND OF THE INVENTION

Interface shear strength, the frictional resistance to movement, is an important parameter utilized in the design and use of geosynthetics. Geosynthetics are planar products manufactured from polymeric material which are used with soil, rock, earth, or other geotechnical engineering materials as an integral part of a man-made project, structure, or system. Geosynthetics include, but are not limited to, geomembranes, geotextiles, geosynthetic clay liners, geogrids, geodrains, and geonets.

Projects that incorporate geosynthetics include earthen structures such as liners and caps for landfills, highway embankments, and earthen dams. The stability of these structures depends, in part, on the shear strength along the interface between the geosynthetic and the material which it contacts usually another geosynthetic or a geomaterial (e.g., soil, rock, concrete, and the like). For the purposes of this application, the term geoengineering materials includes, but is not limited to, geosynthetics and geomaterials. Stability is of particular concern when geosynthetics are used on slopes. For example, a sliding failure will occur if the sliding force due to the weight of material exceeds the frictional resistance between the material and the geosynthetic upon which it rests. Referring to FIG. 1, a sectional view through a waste containment system 1, illustrates a sliding failure. The waste containment system 1 includes a lining system 2 upon which the waste is stored. A sliding failure is depicted by the change in the initial slope of waste 3 to the failed slope of waste 4.

Interface shear strength information for use in geotechnical engineering is typically derived from laboratory tests. Traditionally, a conventional direct shear device was employed in laboratory testing of geosynthetic interface shear strength. See FIG. 2. See also, American Society for Testing and Materials (ASTM) standard test method D3080-90. The direct shear device(s) consists of an upper and lower specimen container 6, 7, both of which are housed in a moveable box 8. Normal loads N are applied to the test specimens 9 through a loading cap 10. The lower specimen holder is fixed to the moveable box 8 which rests on bearings 11. Horizontal movement of the upper specimen container 6 is restricted from movement in the shear load direction S by the reaction arm 12. Shear resistance or strength is measured by determining the amount of force exerted on the movable box 8 prior to movement at the interface 13 of the lower specimen holder 7 and the upper specimen holder 6. As moveable box 8 is horizontally displaced at a constant rate, the upper and lower specimen holders 6, 7 are displaced at the interface 13. This displacement is referred to as shear displacement or shear deformation.

Because conventional direct shear devices were designed to test geomaterial and other particulate matter, modifications are needed for the testing of geosynthetics. For example, the diameter of test specimens typically range between 60 and 100 mm. However, some geosynthetics contain large scale features which are not adequately represented in such small specimen sizes. Consequently, most interface strength testing is currently performed using a direct shear device which includes modifications to accept geosynthetics (See ASTM standard test method 5321-92). This device is essentially a larger version of the device described in ASTM D3080-90 with a recommended diameter of test specimen up to 300 mm.

Direct shear devices allow for the measurement of interface shear strength at different normal loads. This is important because the interface shear strength varies with normal loads. In addition, a direct shear device may detect the change in interface shear strength as movement occurs along the interface. Typically, as movement occurs, shear strength will increase to a peak shear strength and then decrease as additional movement occurs. Eventually, the shear strength will remain constant with additional movement. This constant is referred to as the residual shear stress. Interface shear stress versus shear displacement is illustrated in FIG. 3.

Direct shear devices present several well known disadvantages. First, movement along the interface produces eccentric loading. Eccentric loading, in turn, results in a non-uniformity of stress over the test area. For example, stress concentrations may form at the leading and trailing edges of the specimen. Moreover, the area of the interface changes with deformation resulting in inaccurate test results. Second, machine friction from bearings and from contact between the specimen holders can be problematic because it's contribution to the resistance along the test interface cannot be distinguished. Third, direct shear devices provide only limited movement along the interface. In contrast, as shown in FIG. 3, a relatively large movement is often necessary to measure the residual strength. Fourth, application of high normal loads is difficult because of the large size of the specimen and the wear on the bearings. Fifth, the direct shear device is expensive because the shear box (e.g., the portion of the device that contains the test specimen) and the mechanisms for applying the normal load and for forcing interface movement are one integral unit. Sixth, the large size of the testing device increases the effort needed to prepare, set up, and test the specimens. The last two items are the primary reasons that interface strength testing of geosynthetics is an expensive process.

SUMMARY OF THE INVENTION

The present invention relates to the measurement of interface shear strength in geosynthetics and geomaterials. An apparatus is provided for measuring a shear strength at the interface between geoengineering materials, having a first, a second, a third, and a fourth surface to which a geoengineering material may be coupled. The first and the second surface are operatively coupled to form an interface with the third and the fourth surface, respectively. A first loading means is provided for exerting a load substantially perpendicular to the interface and a second loading means is provided for exerting a load substantially parallel to the interface.

A further embodiment of the present invention is a method of measuring a shear strength at the interface between geoengineering materials. The method includes the steps of coupling a geoengineering material to a first, a second, a third, and a fourth surface; positioning the first and the second surface adjacent the third and the fourth surface, respectively, to form an interface therebetween; loading the first and the second surface to create a load substantially perpendicular to the third and the fourth surface, respectively; and propelling the first and the second surface substantially parallel to the third and the fourth surface, respectively.

DESCRIPTION OF THE PREFERRED EMBODIMENTS

Preferred embodiments of the invention will now be described with reference to the accompanying figures. The present invention generally comprises a double-interface shear device for measurement of interface strength between geosynthetics and geomaterials. The device provides for the convenient application of normal loads, for the measurement of interface strength prior to and following deformation along the interface, and for the measurement of volume changes of the specimen normal to the interface.

However, the following description of the apparatus and methods are not intended to be limiting in any manner; they are merely illustrative. Various modifications, applications, and changes may occur to those skilled in the art, without departing from the true spirit and scope of the invention.

Figure 1:
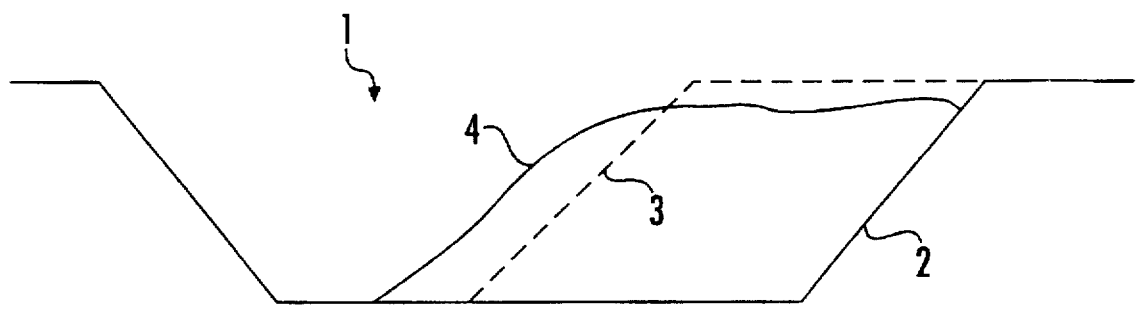
FIG. 1 is a cross section of a slope in a waste containment system.
Figure 2:
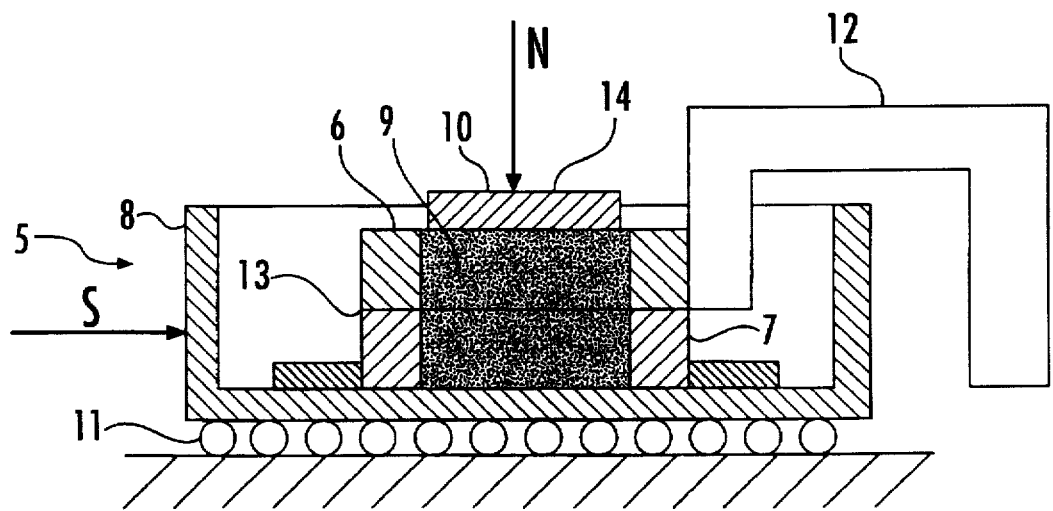
FIG. 2 is a drawing of a conventional direct shear device.
Figure 3:
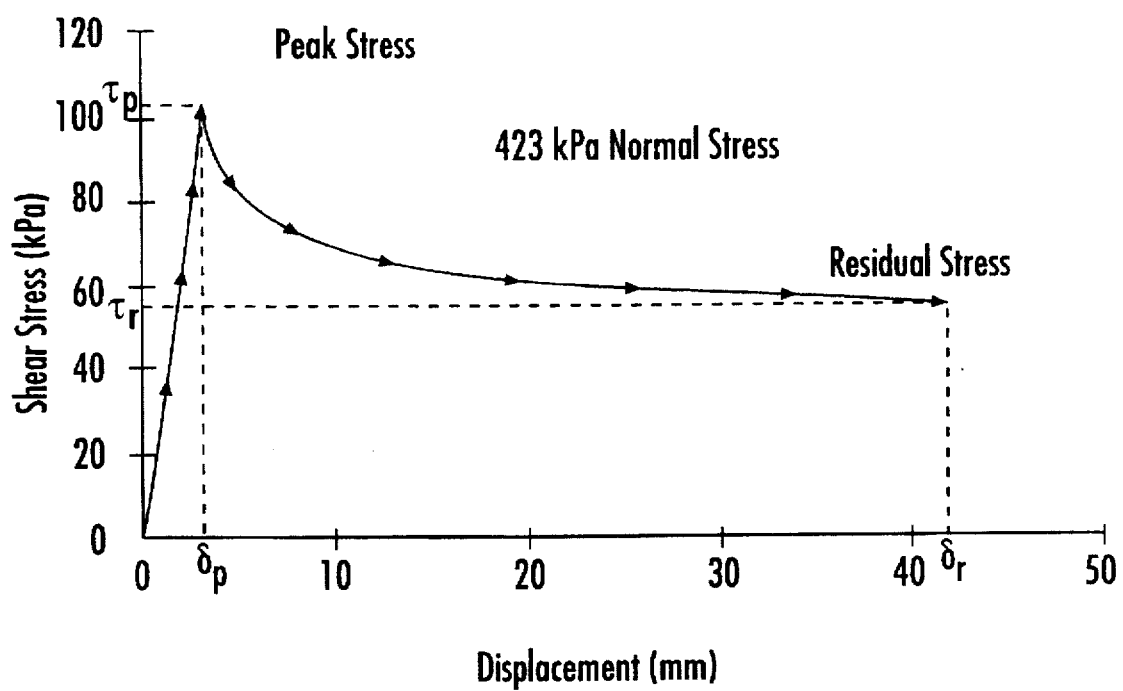
FIG. 3 is a graph of shear stress versus displacement for an interface between a non-woven geotextile and smooth geomembrane.
Figure 4:
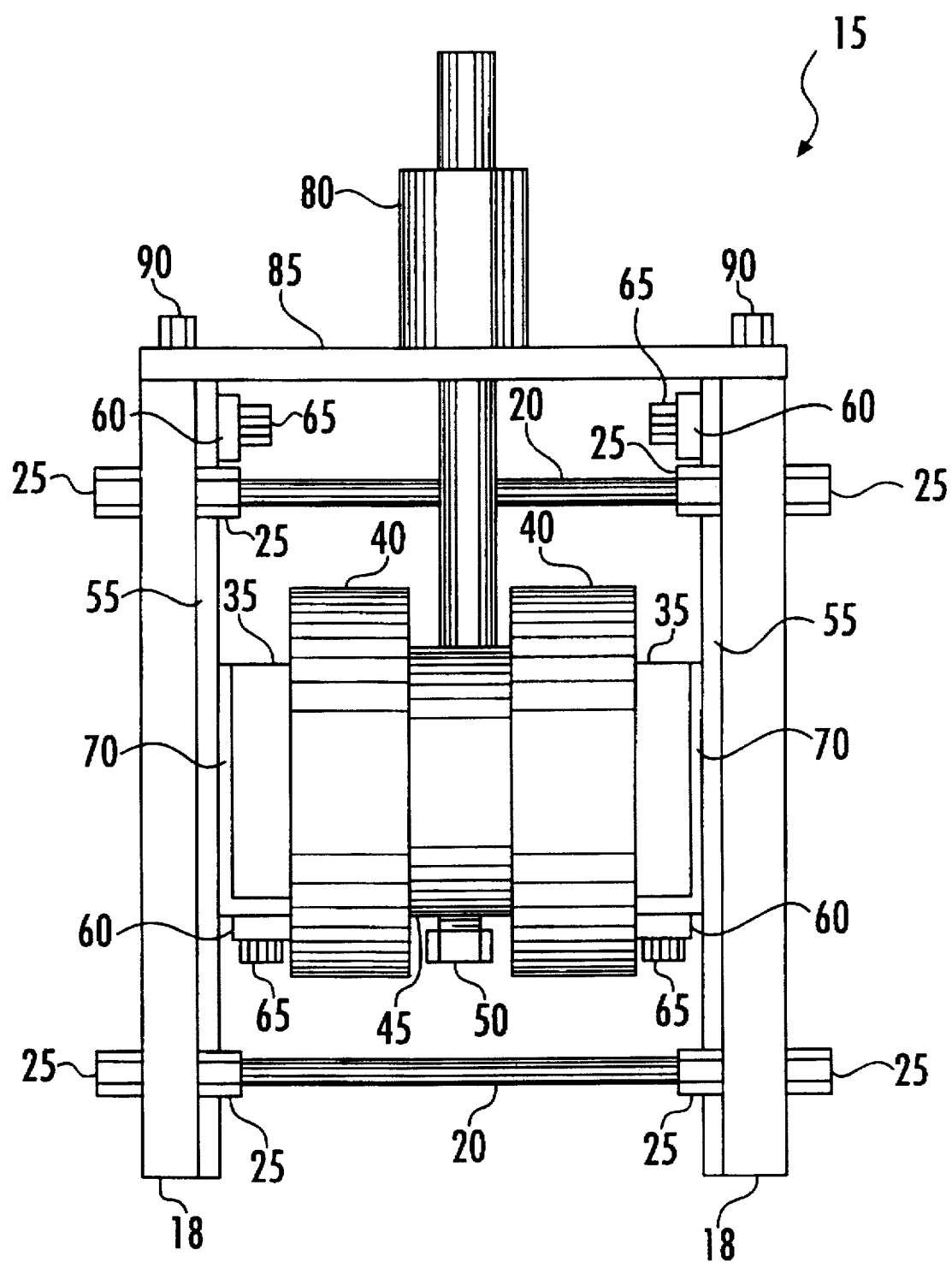
FIG. 4 is a front view of a double-interface shear apparatus.
Figure 5:
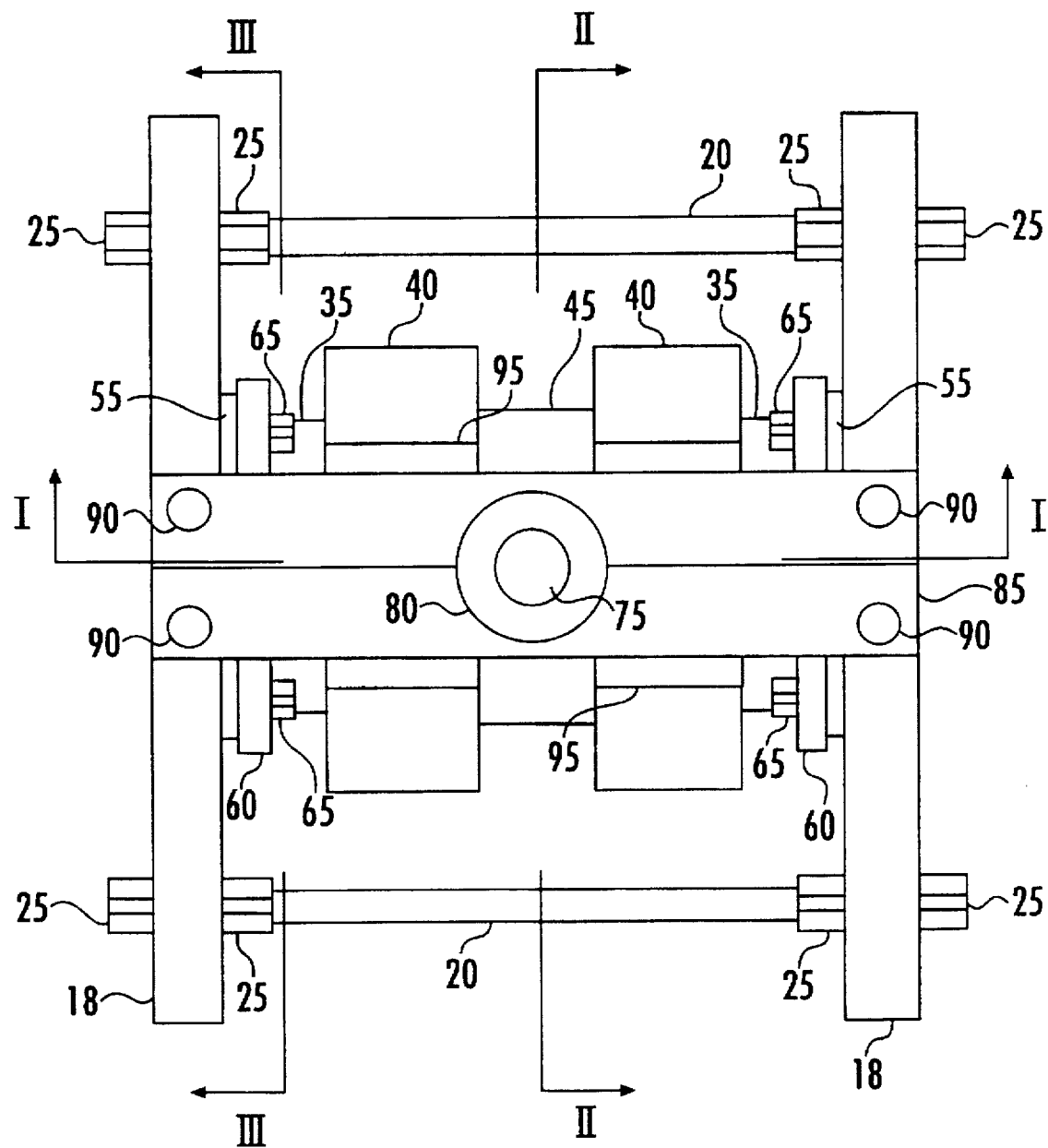
FIG. 5 is a top view of a double-interface shear apparatus.
Figure 6:
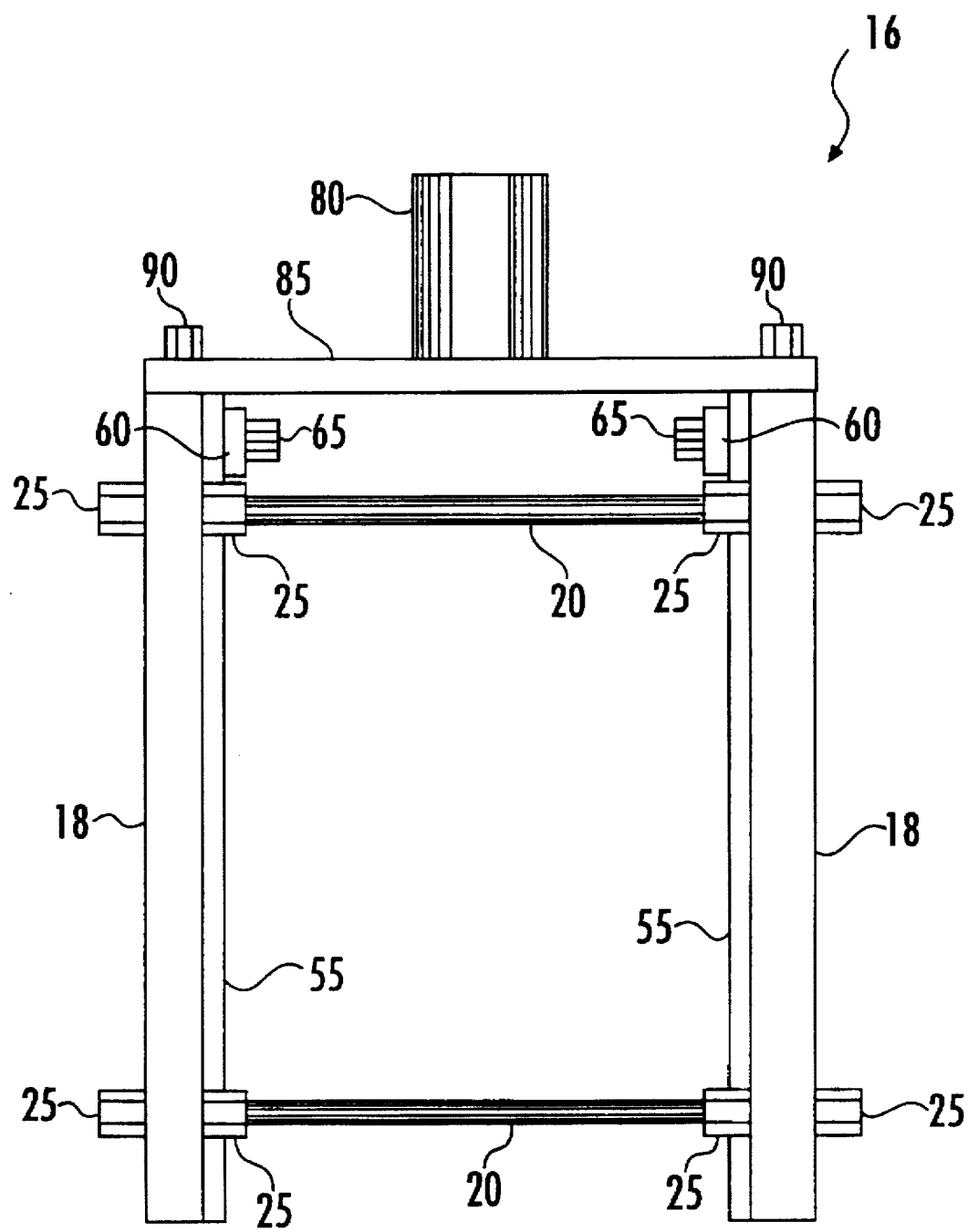
FIG. 6 is a front view of an outer assembly of a double-interface shear apparatus.
Figure 7:
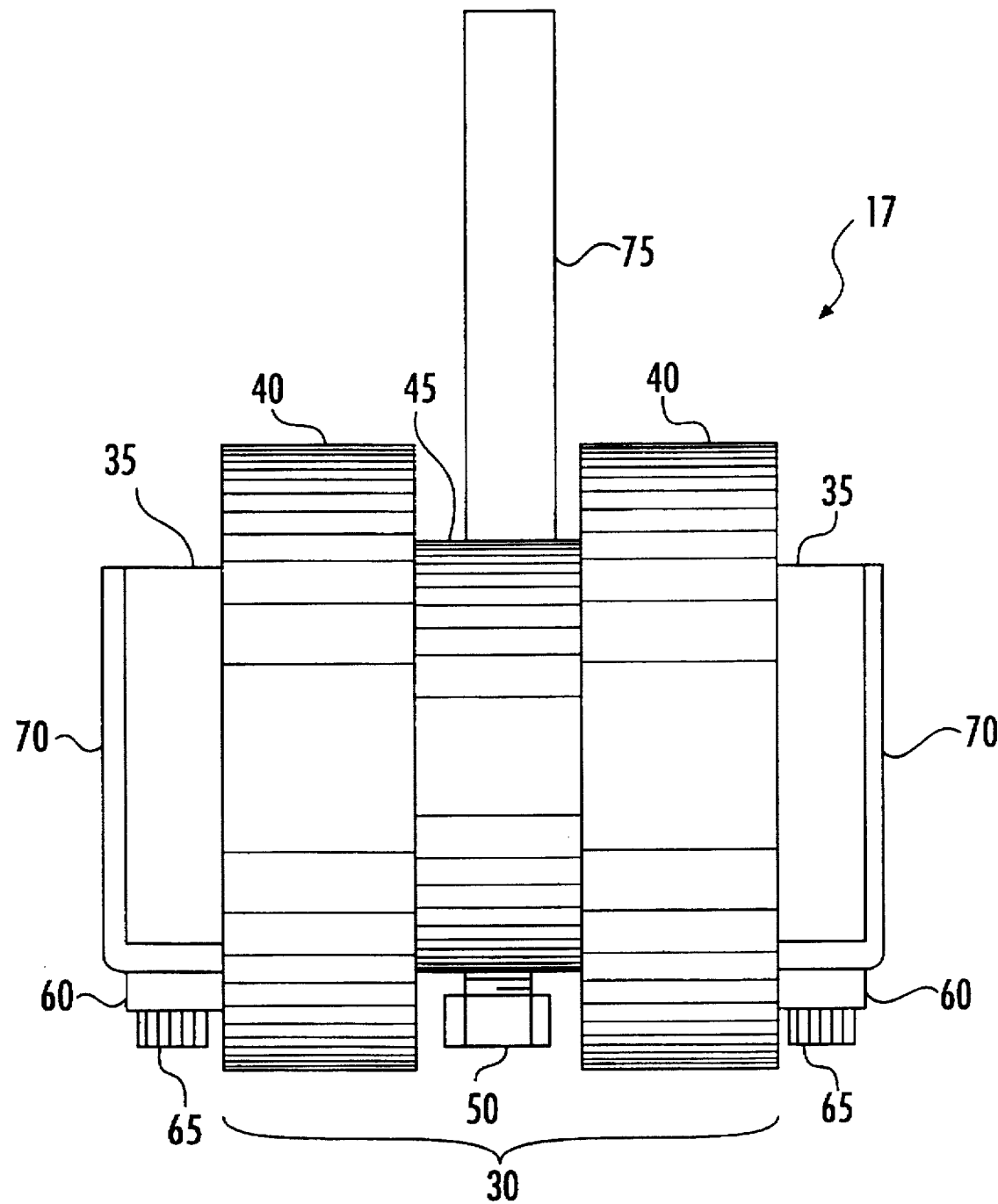
FIG. 7 is a front view of an inner assembly of a double-interface shear apparatus.
Figure 8:
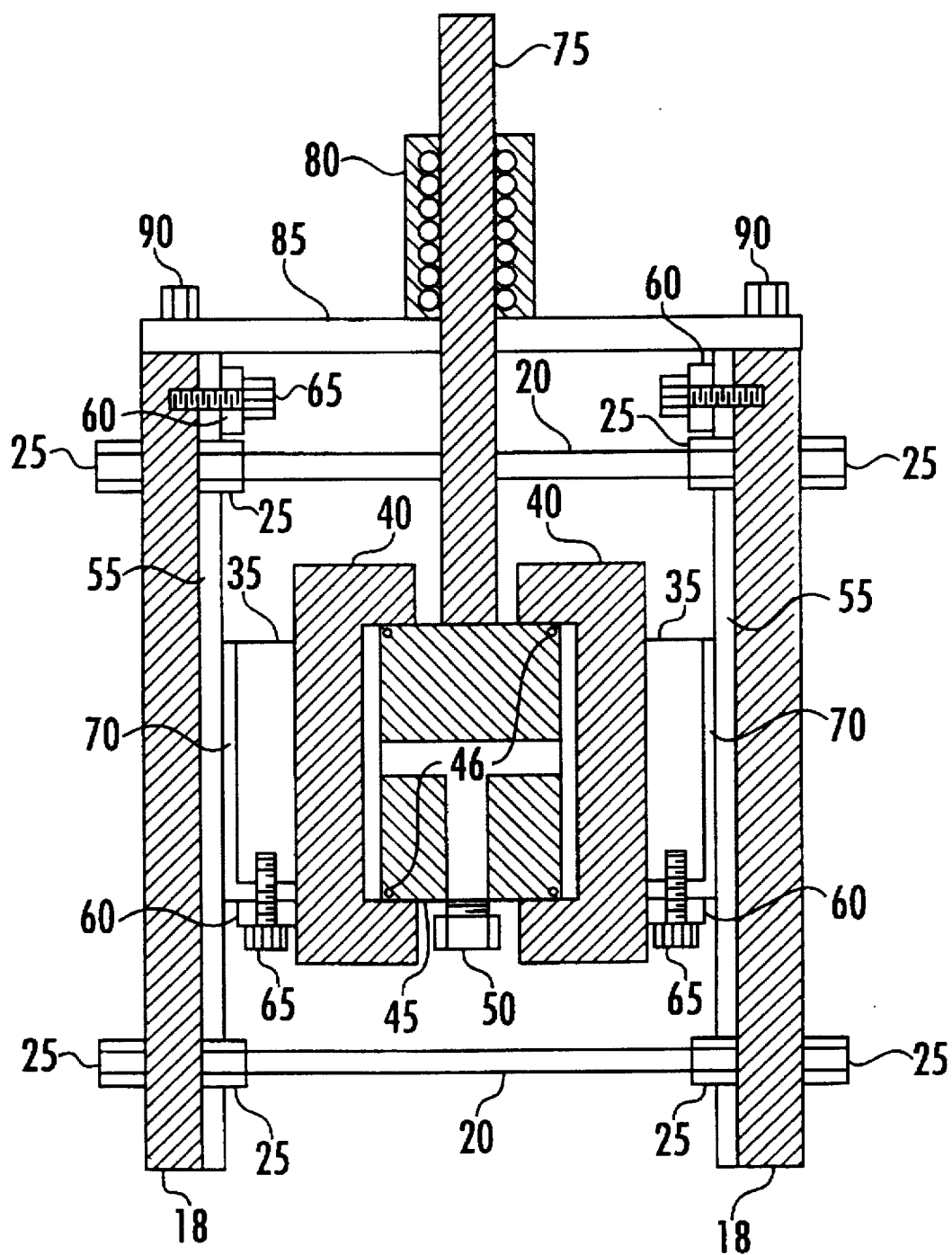
FIG. 8 is a view of section I—I of FIG. 5.

Referring to FIGS. 4–7, double-interface shear apparatus 15 of the present invention comprises an outer assembly 16 (see FIG. 6) and an inner assembly 17 (see FIG. 7). The outer assembly 16 is comprised of two rigid outer load plates 18, coupled substantially parallel to each other by the tie rods 20 and tie rod nuts 25. The rods 20 are also substantially parallel to each other. The dimensions and materials from which the outer load plates 18 and the tie rods 20 are constructed may vary depending upon the material being tested and the loads being applied. The outer test specimens 55 are attached to the outer load plates 18 with specimen clamps 60 and clamp bolts 65 (see FIG. 4).

The inner assembly 17 comprises a double-piston cylinder 30 and two inner load plates 35. The inner load plates 35 are coupled to the piston heads 40, which in turn slide on the cylinder body 45 ends. The cylinder body 45 has a pressure port 50 into which pressure can be introduced to push the piston heads 40 outward. Pressure within the cylinder 30 may be maintained by o-rings 46, or by other pressure containing devices. The size and shape (e.g., circular, rectangular, or square) of the inner bearing plates 35 may vary with the desired application. Likewise, the piston heads 40 may vary in size and shape depending upon the desired applications. Moreover, the piston heads 40 can be external or internal (not shown) to the cylinder body 45. Two identical inner test specimens 70 from a sample of a second geosynthetic material are attached to the inner bearing plate 35 faces with specimen clamps 60 and clamp bolts 65.

Assembly of the Double-Interface Shear Apparatus

Figure 9:
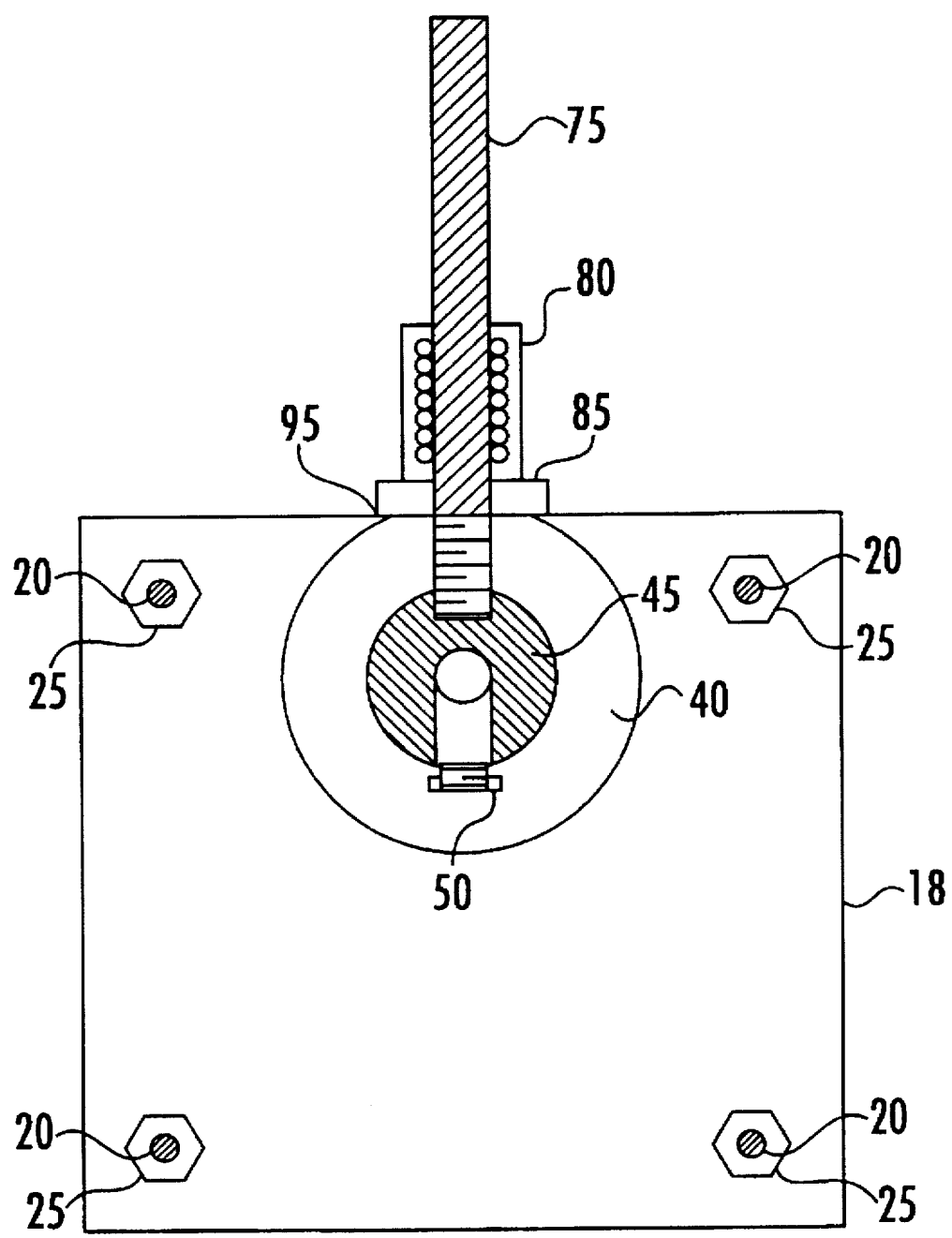
FIG. 9 is a view of section II—II of FIG. 5.

The outer assembly 16 surrounds the inner assembly 17 such that the loading rod 75 passes through an alignment bushing 80. Alignment bushing 80 contains bearings 81 to facilitate resistance-free movement. The alignment bushing 80 is attached to an alignment bracket 85, which in turn is coupled to the outer load plates 18 with bracket bolts 90. Alignment of the inner load plates 35 is facilitated by flats 95 machined on the piston heads 40. Once the loading rod 75 has been attached to the cylinder body 45, the inner assembly 17 can be pulled upward so that the flats 95 on the piston heads 40 press on the bottom side of the alignment bracket 85, (see FIG. 9). Pulling the inner assembly 10 upward rotates the piston heads 40 such that the inner bearing plates 35 are aligned with each other. In addition, the faces of the geosynthetic specimens 55 and 70 clamped to the inner bearing plates 35, are centered and parallel to the faces of the geosynthetic material 55 clamped to the outer load plates 18. The piston heads 40 are rotated so that the flats 95 are parallel with the bottom face of the alignment bracket 85.

The double-sided piston 30 is pressurized so that the piston heads 40 move outward and geosynthetic test materials 55, 70 are pressed between the inner bearing plates 35 and the outer bearing plates 18. The piston pressure may be adjusted to obtain the desired normal pressure.

Specimen Preparation

Specimens for testing are cut from the geosynthetic for which interface strength information is desired. The outer test specimen 55 has a length slightly less than the length of the outer load plates 18 and a width slightly greater than the width of the inner load plates 35. The inner test specimen 70 has a length slightly longer than the length of the inner load plates 35 and includes a portion which may be clamped to the lower edge of the inner load plate 35.

Figure 10:
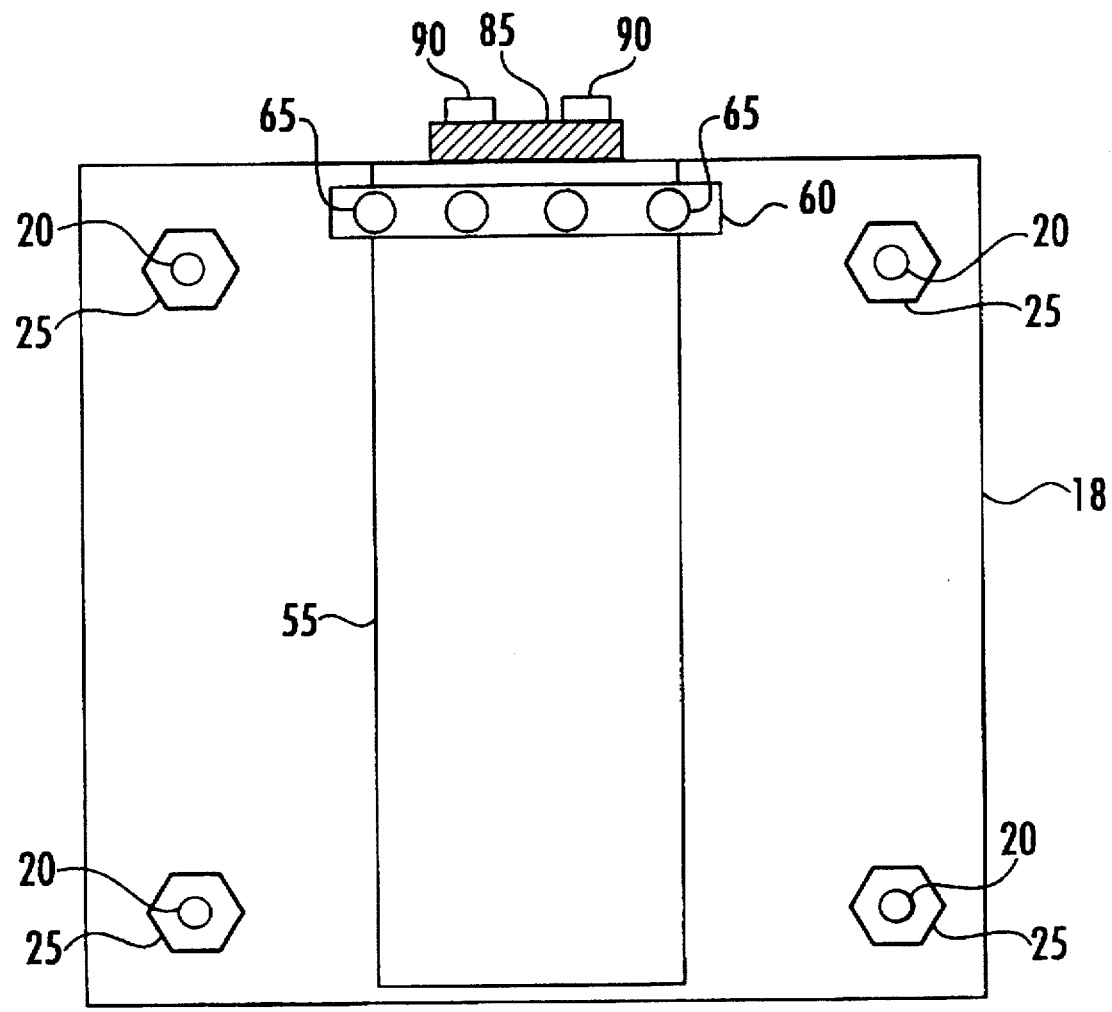
FIG. 10 is a view of section III—III of FIG. 5.
Figure 11:
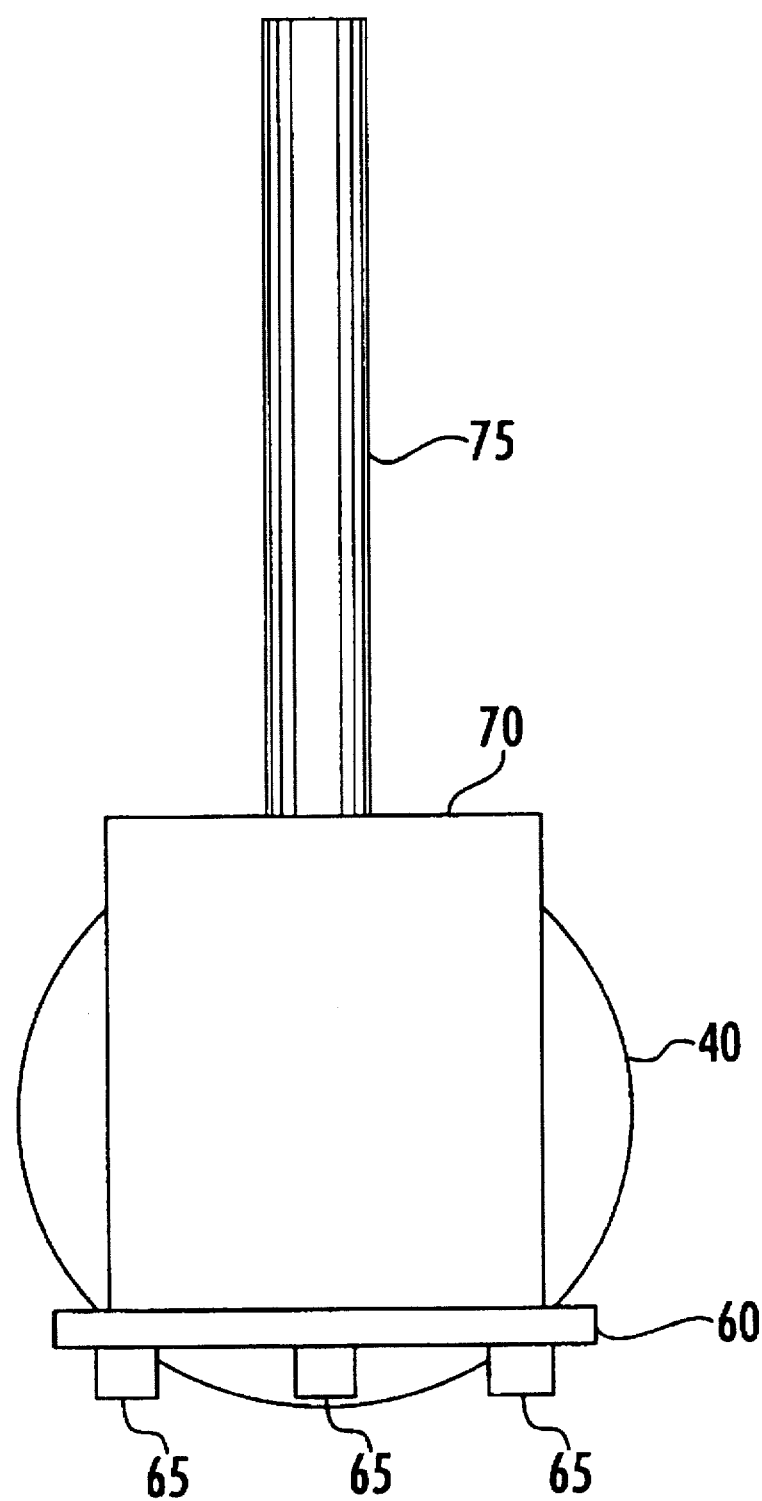
FIG. 11 is an end view of an inner assembly.

Specimens 55, 70 may be mounted in several ways. The specimens can be mounted directly to the bearing plates with clamps, (see FIGS. 10 and 11). Where it is desirable to minimize or eliminate slippage between the geosynthetic and the bearing plates 18, 35, the surface of the bearing plates may be roughened or a thin, roughened plate may be attached to the bearing plates prior to attaching the geosynthetic specimens. Specimens may also be attached to the mounting plates with staples, glue or the like and then attached to the bearing plates 18, 35.

Assembly of the Double-Interface Shear Apparatus into a Convention Load Press

The following procedure corresponds to the use of a conventional load press 110 for generating shear deformation along the test interface.

Figure 12:
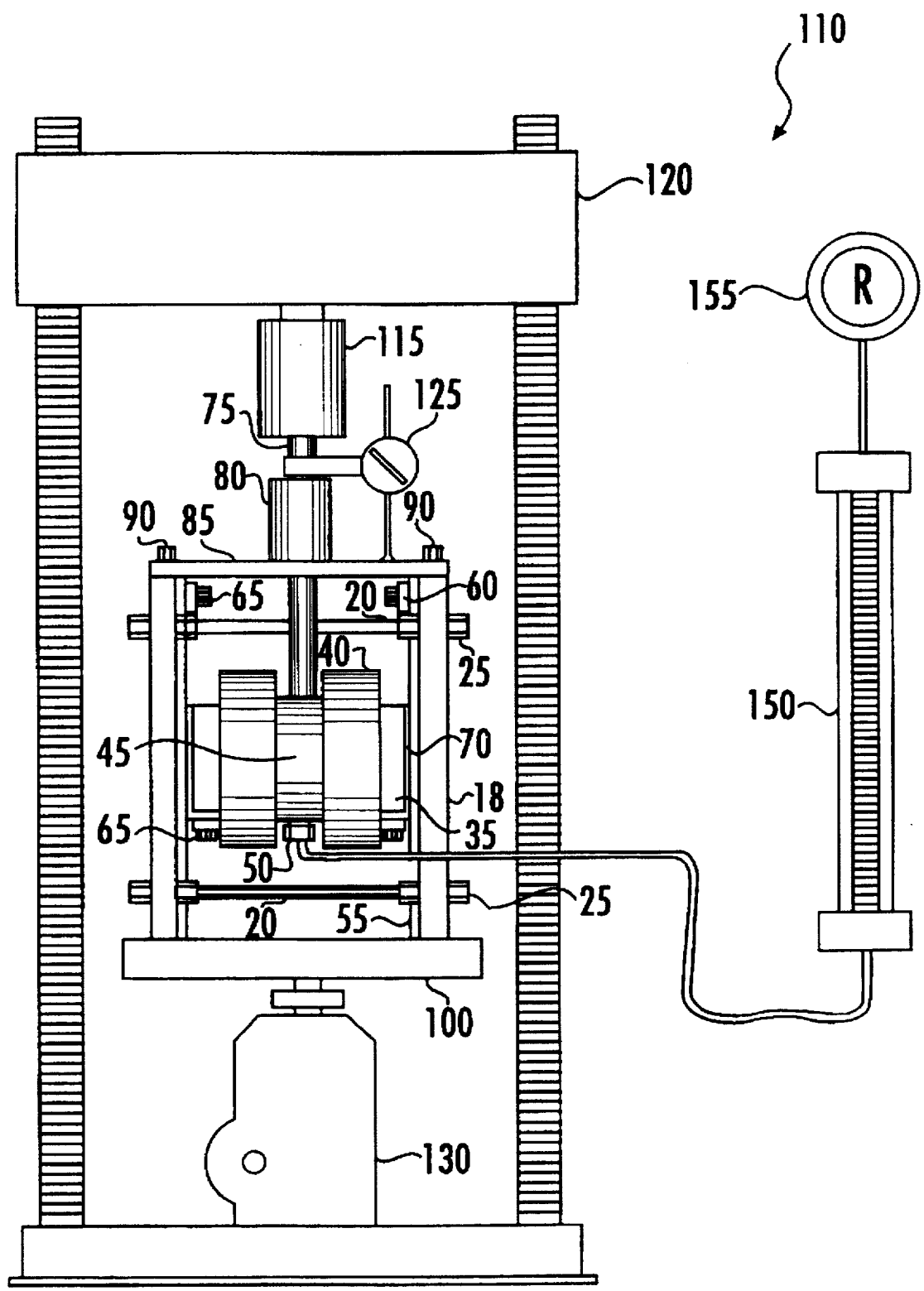
FIG. 12 is a view of a double-interface shear apparatus in a conventional load press.

The double-interface shear device is positioned on the platen 100 of the load press 110, (see FIG. 12). The platen 100 is raised by activating the motorized screw jack 130 such that the loading rod 75 can be coupled to the load cell 115, which in turn is coupled to the crosshead 120. A pressure port 50 on the double-sided piston 30 is vented to atmosphere and the piston heads 40 contracted to create a gap between the inner and outer geosynthetic specimens 55, 70. The inner assembly 17 is hanging from load cell 115 and its weight can be determined and tared. A small seating pressure is then applied to the pressure port 50 of the double-sided piston 30, causing the piston heads 40 to move outward such that the inner and outer test specimens 55, 70 contact each other.

Normal Load Application

Normal loads, usually specified in terms of a normal stress, are applied to the test specimens by pressurizing the double-sided piston 30. The pressure required in the double-sided piston 30 to effectuate a desired normal load can be calculated by measuring the area of the inner bearing plates 35 and the effective area of the piston heads 40. Once calculated, the appropriate pressure is applied by pressure regulator 155 through the pressure port 50.

Measurement of Interface Strength

Interface shear strength is determined by measuring the load transmitted to the load cell 115 as the platen 100 is raised. After a platen speed has been selected, a zero or reference reading for the load cell 115 and dial gauge 125 is recorded. The motorized screw jack 130 is then activated so that the platen 100 moves upward at the desired speed. Load cell 115, buret 150 and dial gauge 125 readings corresponding to shear load S, normal load N and shear displacement respectively are recorded. From the measurements a plot of shear stress versus shear displacement may be generated. Testing is continued until a predetermined amount of shear deformation has occurred or the residual strength has been reached. Testing is terminated for a particular normal load by turning off the motorized screw jack 130 to stop the platen 100 movement. Typically interface shear strength is measured at several normal loads by repeating the above-described process at the additional normal loads.

Alternative Loading Procedures

Figure 13:
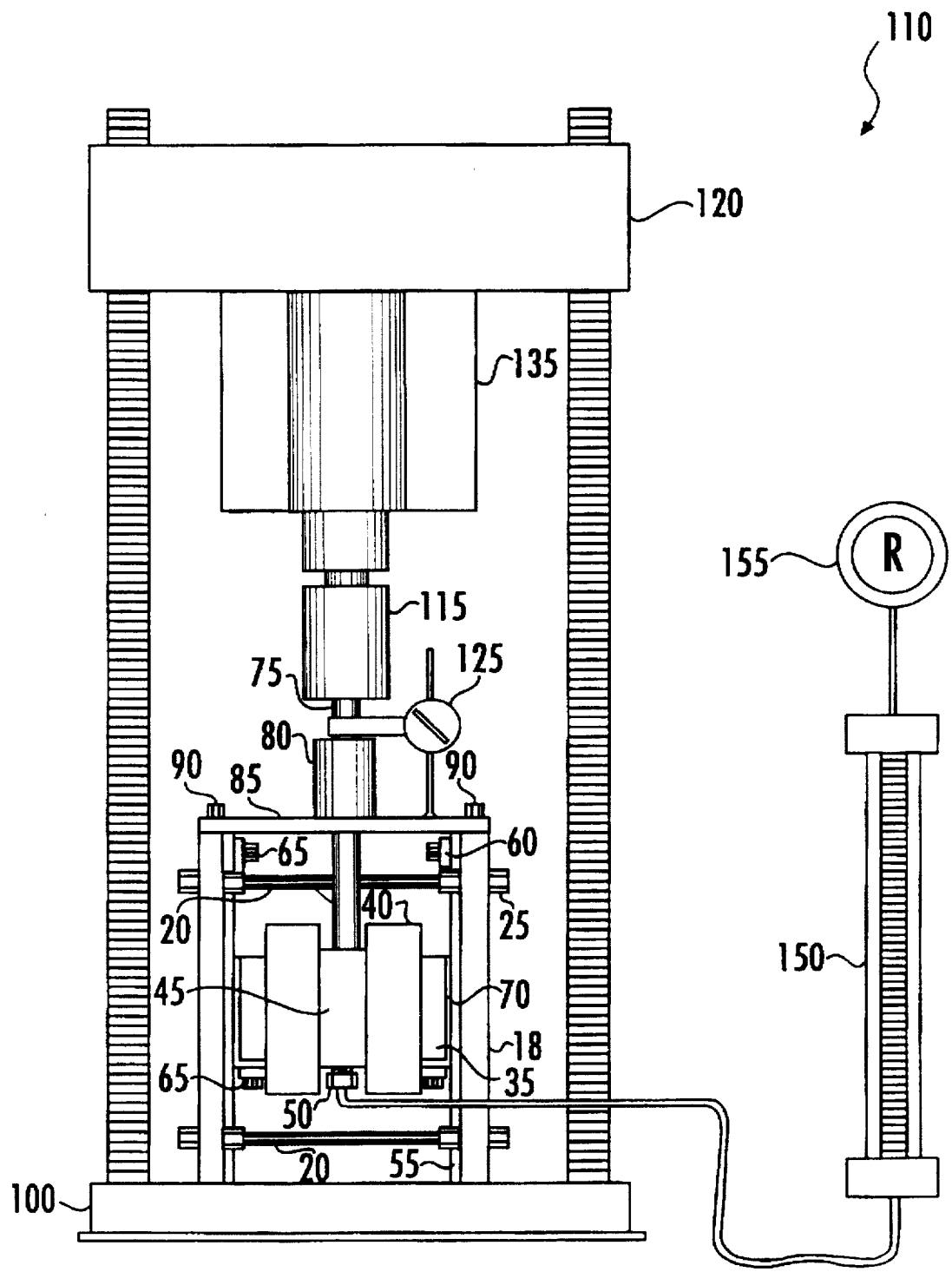
FIG. 13 is a view of the double-interface shear apparatus in a load press having an air piston or hydraulic actuator.
Figure 14:
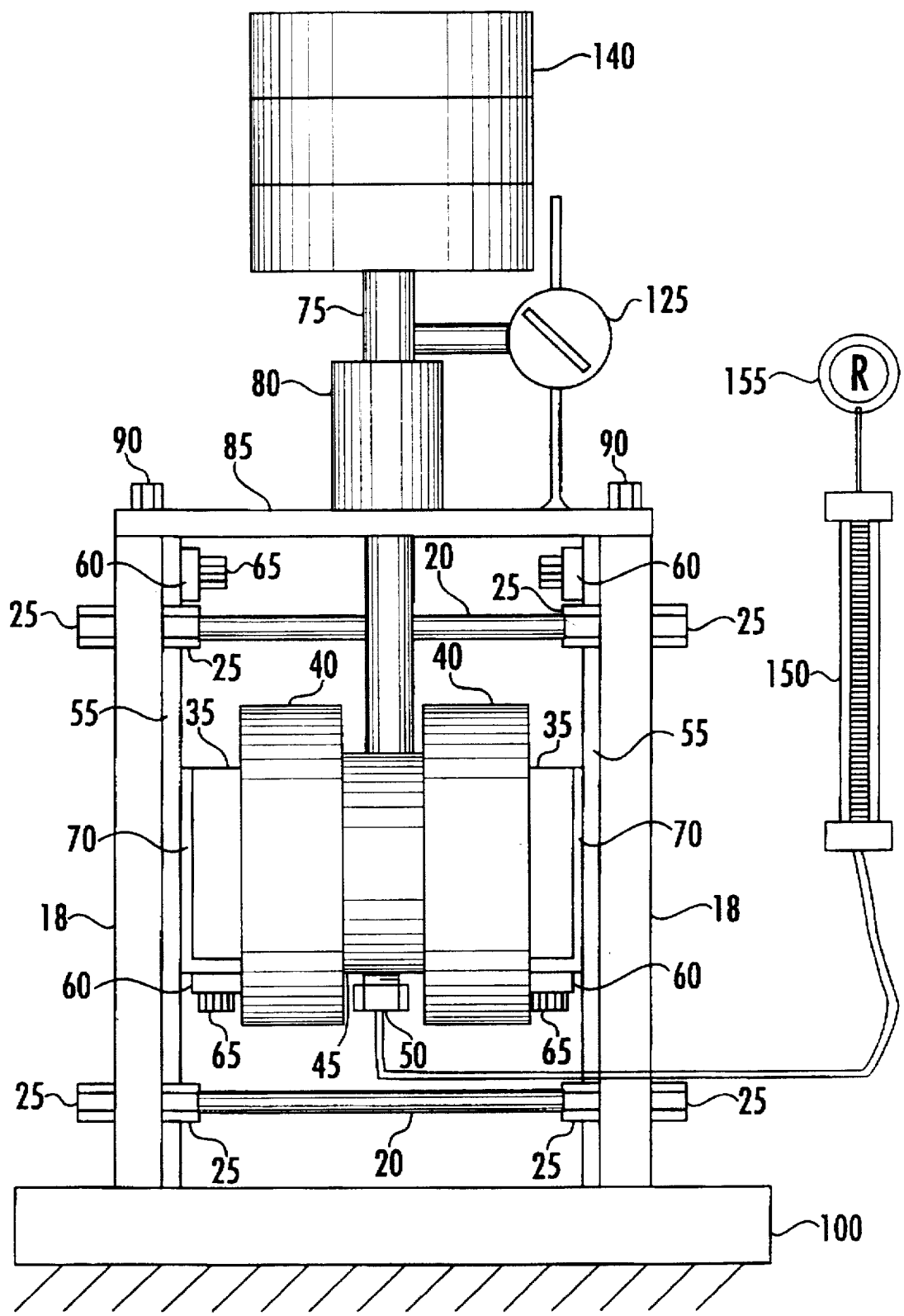
FIG. 14 is a view of the double-interface shear apparatus with shear load applied by stacking weights on the loading rod.

The load press 110 described above can be modified so that an air piston or hydraulic actuator 135 can be used to promote shear deformation (see FIG. 13). Alternatively, long-term shear strength tests (sometimes referred to as "creep" tests) can be performed by stacking or hanging weights 140 on the loading rod 75 as shown in FIG. 14. The advantage of these loading schemes is that a series of constant loads can be applied to the loading rod 75 and maintained for long periods of time.

This loading technique is useful for determining the creep behavior or long-term shear deformation characteristics of specimens subjected to a constant shear load.

Measurement of Interface Strength Between Geosynthetics and Geomaterials

Figure 15:
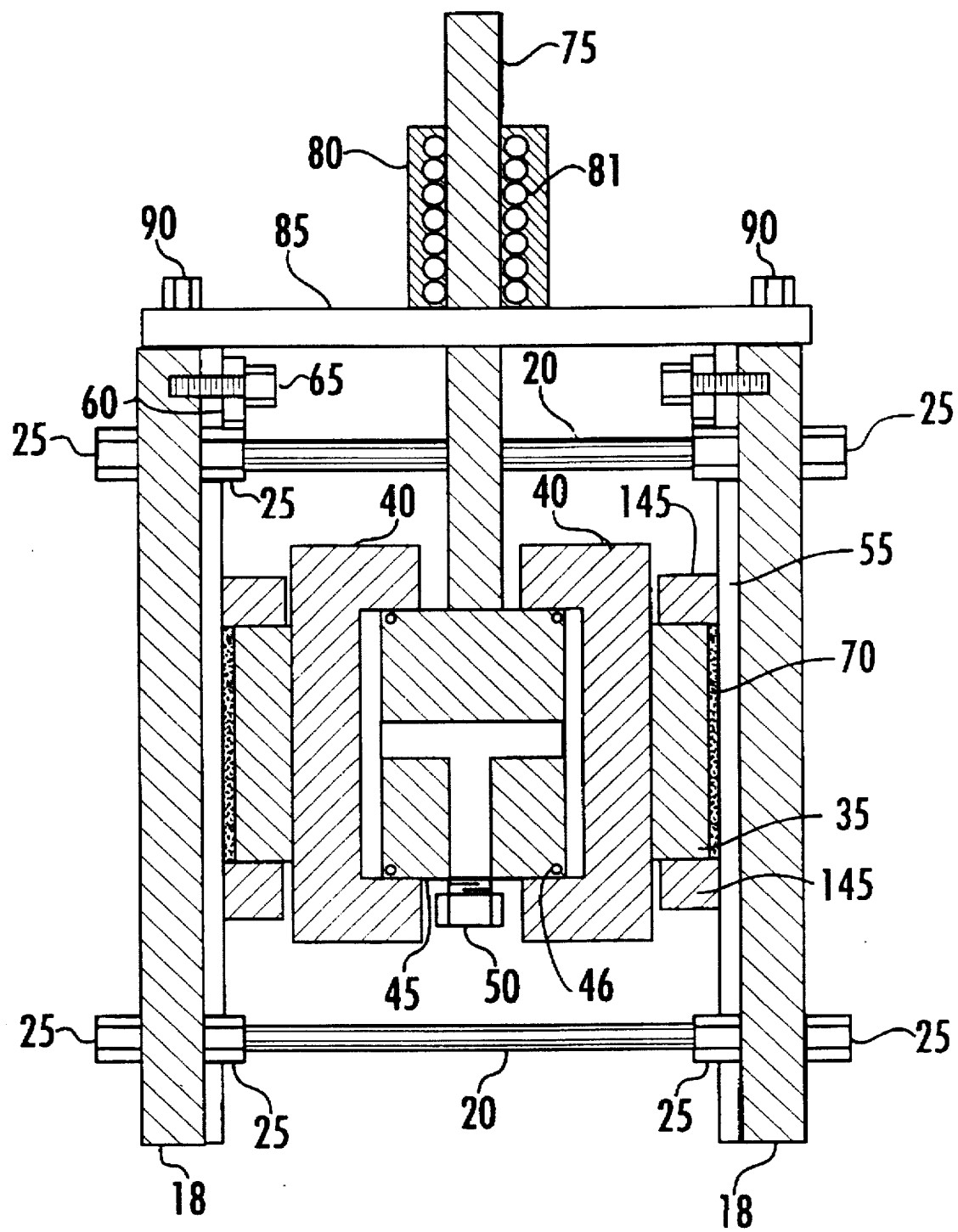
FIG. 15 is a view of section I—I of FIG. 5 illustrating the use of containment rings for testing geomaterial.

Interface strength between geosynthetics and geomaterials is determined with the present invention by using a containment ring 145 for the geomaterial as shown in FIG. 15. The geosynthetic test specimen 55 is attached to the outer bearing plate 18 as described above. The geomaterial 70 is packed into the containment ring 145 which is coupled to the inner bearing plate 35. The tolerance of the inner dimensions of the containment ring 145 and the outer dimensions of the inner bearing plate 35 allows the containment ring 145 to slide over the inner bearing plate 35, but prevents extrusion of the geomaterial 70 as normal loads are applied.

Normal Deformation Measurements

Deformations of the test material during application of the normal load and during shear deformation can be measured using the configuration shown in FIG. 12. The void space in the double-sided piston 30 and tubing connected between the inlet port and a buret 150 is filled with liquid. The volume of liquid in the assembly is adjusted so that the liquid/air interface occurs in the buret 150. A buret 150 reading is recorded and used as a zero reference before application of normal loads or before shear deformation occurs. If the test specimens undergo normal deformation, the piston heads 40 will move in or out to compensate for this and the position of the liquid/air interface will move. Normal deformations can be calculated from volume changes measured with the buret 150 and measured area of the inner bearing plates 35.

Specimen Saturation

Figure 16:
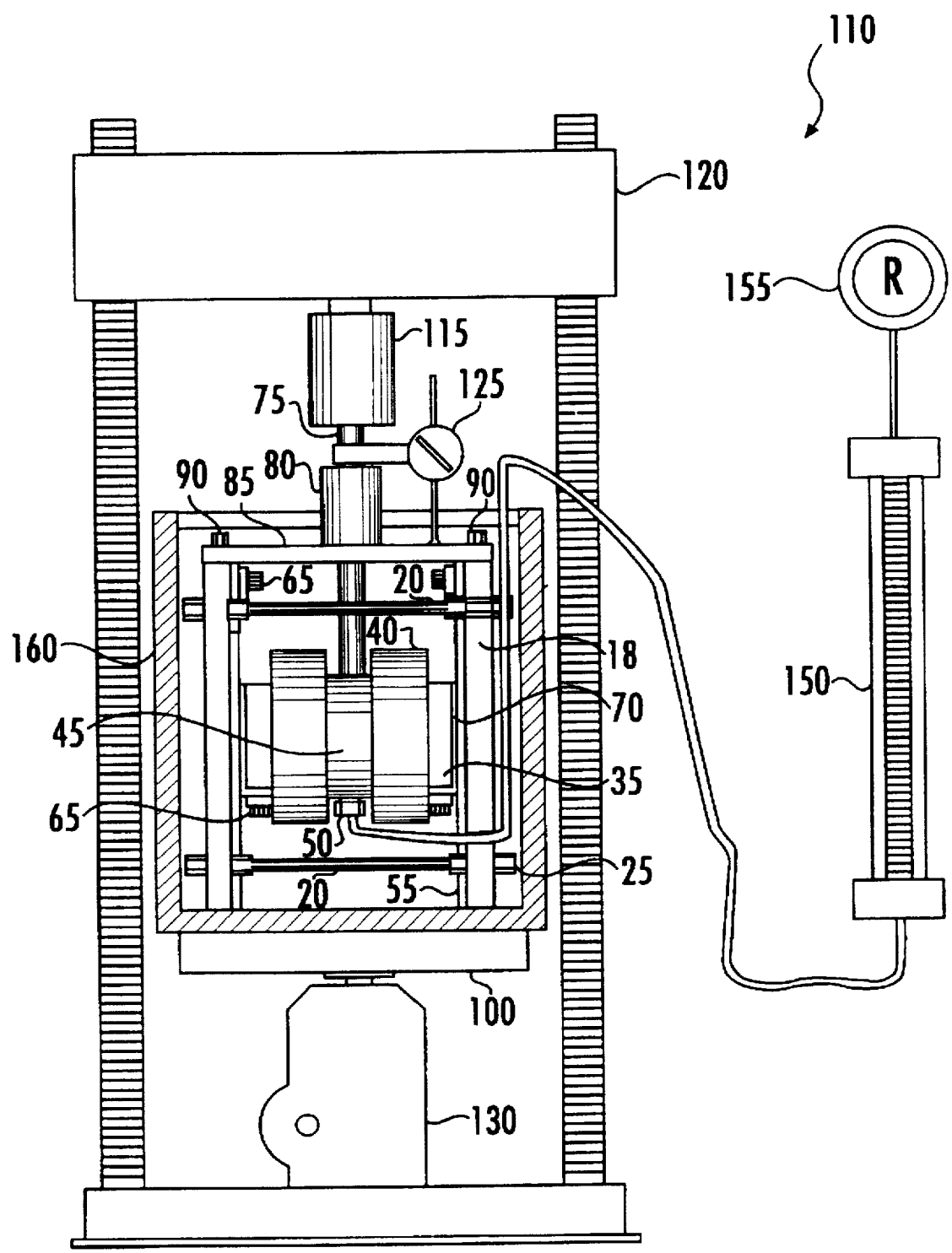
FIG. 16 is a view of the double-interface shear apparatus in a tank of liquid in a conventional load press.

Interface shear strength can vary depending on whether or not the test specimens are saturated with liquid. Saturating the specimens using the present invention is accomplished by inserting the entire device in a tank 160 of water and then placing the tank 160 in the load press 110 as shown in FIG. 16.

EXAMPLE I

Measurement of interface strength between a high density polyethylene geomembrane and a non-woven, needle-punched geotextile.

The interface strength between a geotextile and a geomembrane was measured in a series of tests performed with the double-interface shear apparatus. The geomembrane consisted of a 1.52-mm thick, smooth geomembrane made of high density polyethylene. The geotextile was a non-woven, needle-punched geotextile with a mass per unit area of 441 g/m$^2$. A shear displacement rate of 1.3 mm/min was used. This interface is of special interest because it formed a portion of the sliding surface in the Kettleman Hills failure (Byrne, R. J., Kendall, J., and Brown, S. (1992) "Cause and Mechanism of Failure, Kettleman Hills Landfill B-19, Unit IA", Proc., *ASCE Spec. Conf. on Performance and Stability of Slopes and Embankments-II*, Vol. 2, pp. 1188–1215). Therefore, considerable testing has already been conducted on this interface using other test methods, and the results have been shown to be consistent with the observed failure mechanism.

Figure 17:
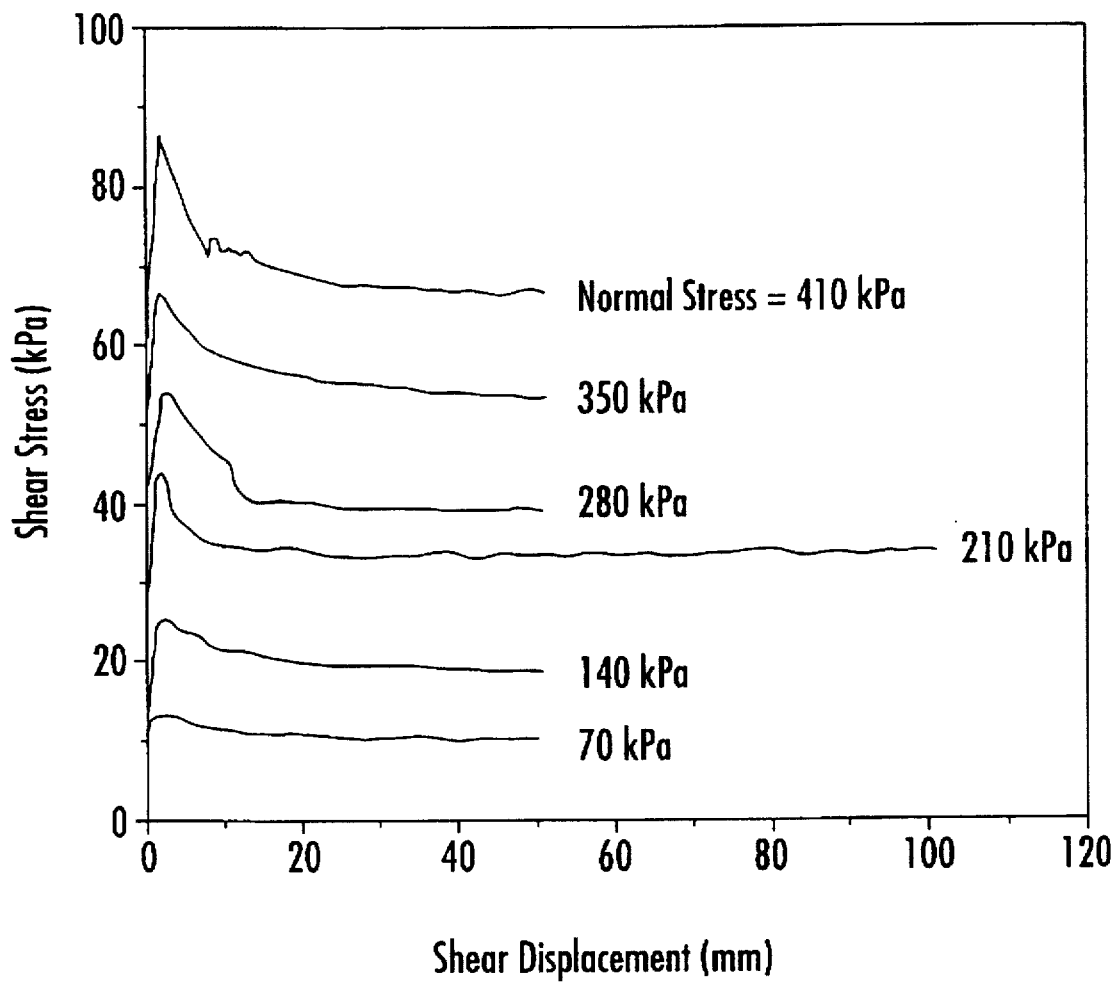
FIG. 17 is a graph of a geotextile/geomembrane interface shear stress versus displacement measured with a double-interface shear apparatus.

A plot of shear stress versus shear displacement from the double-interface shear device tests is shown in FIG. 17 for 6 normal stresses ranging from 70 kPa to 410 kPa. Peak shear stresses were mobilized at about 2.5 mm of displacement, and there were significant reductions in shear stress with continued displacement. Residual shear stresses were reached at approximately 20 mm of displacement. However, relative displacements up to 200 mm are possible with this prototype. The measured residual strength averaged 75 percent of the measured shear stresses.

Figure 18:
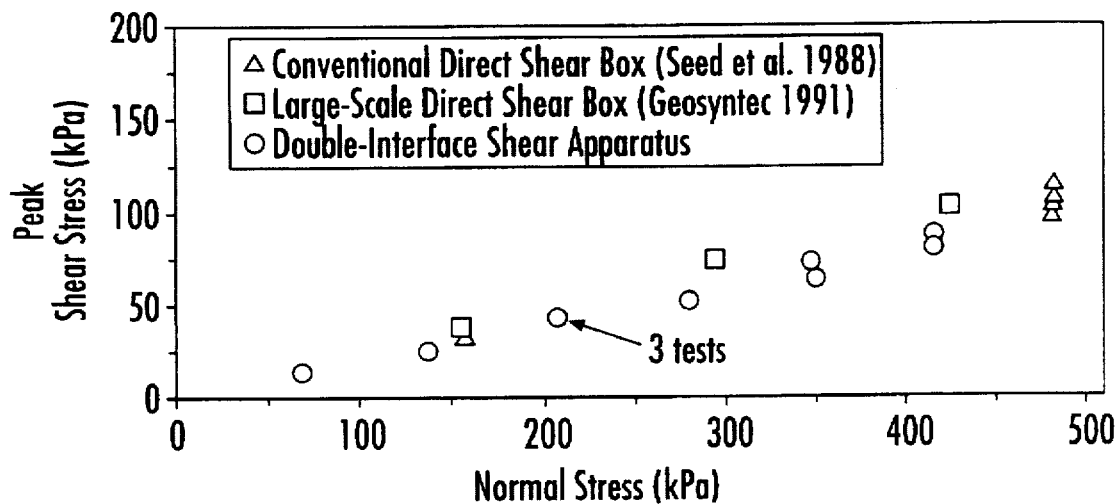
FIG. 18 is a graph of geotextile/geomembrane interface peak shear stress versus normal stress.
Figure 19:
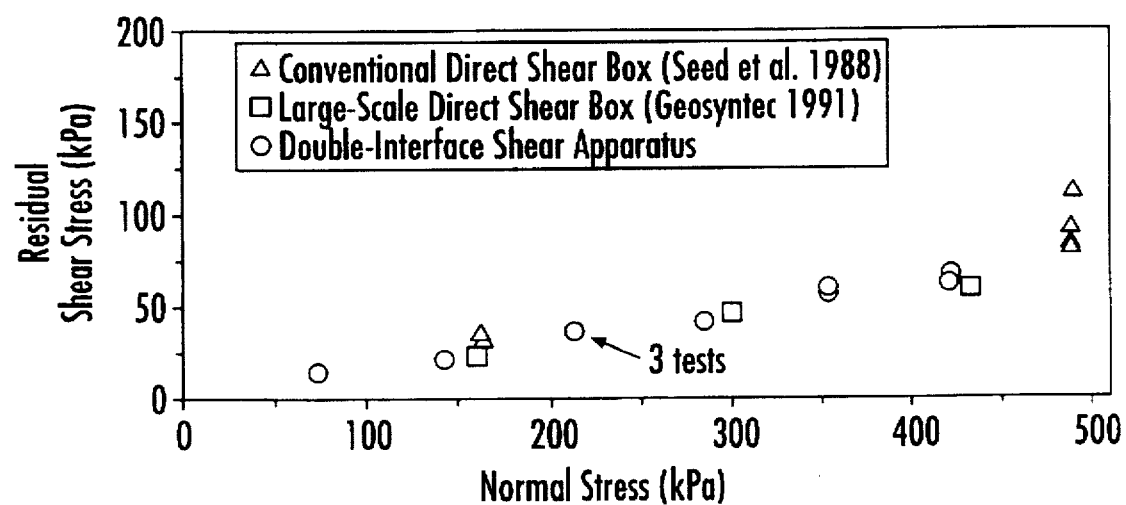
FIG. 19 is a graph of geotextile/geomembrane interface residual shear stress versus normal stress.

Peak and residual shear stresses from FIG. 17 are plotted versus normal stress on FIGS. 18 and 19, respectively. The ability to reproduce results with the double-interface shear device was investigated by performing several tests at a given normal stress, and these data are also plotted on FIGS. 18 and 19. The results are consistent at each normal stress. In addition, the double-interface shear device test results were compared with results from other test methods. Seed et al. (Seed, R. B., Mitchell, J. K. and Seed, H. B. (1988) "Slope Stability Failure Investigation: Unit B19, Phase I-A, Kettleman Hills, California", Research Report No. UCB/GT/88-01, University of California, Berkeley, Calif.) conducted conventional direct shear tests on this geotextile/geomembrane interface, while Geosyntec performed largescale direct shear tests (Geosyntec (1991) "Draft Final Report, Landfill Unit B-19, Phase IA Investigation, Kettleman Hills Facility, Kettleman City, Calif.", Report Prepared for Chemical Waste Management, Inc. by Geosyntec Consultants, Atlanta, Ga.). Both sets of direct shear test results are included with the double-interface shear device results in FIGS. 18 and 19. All the results compare favorably.

What is claimed is:

1. An apparatus for measuring a shear strength at an interface between geoengineering materials, comprising:

an outer assembly having outer lead plates for coupling a first geoengineering material;

an inner assembly having a multi-piston cylinder, each piston having an inner lead plate for coupling a second geoengineering material, the inner assembly positioned within the outer assembly;

interfaces formed by operatively coupling the inner and outer lead plates;

a loader for producing a load normal to the interfaces; and a shearer for producing a force substantially parallel to the interfaces.

2. A method of measuring a shear strength at an interface between geoengineering materials, comprising the steps of:

coupling a first geoengineering material to outer load plates of an outer assembly;

attaching a second geoengineering material to inner load plates of an inner assembly, the inner load assembly having a multi-piston cylinder, each of the inner load plates coupled to one of the pistons;

positioning the inner assembly within the outer assembly so that the inner and outer load plates are adjacent one another to form interfaces therebetween;

applying a load substantially perpendicular to the interfaces; and creating a force substantially parallel to the interfaces.

3. The method of claim 2 further comprising the step of:

repeating the steps of coupling, positioning, applying and creating at a variety of loads.

4. The method of claim 2, further comprising the step of:

immersing the fixed and the mobile surfaces in a liquid.

5. The method of claim 2, further comprising the step of:

measuring a linear displacement at the interfaces.

6. The method of claim 2, further comprising the step of:

measuring a normal deformation at the interfaces.

7. The method of claim 2, further comprising the step of:

measuring the load at the interfaces.

8. The method of claim 2, further comprising the step of:

measuring the force at the interfaces.

9. The apparatus of claim 1 wherein said loader is a pneumatic pressure source, a hydraulic pressure source, or a combination pneumatic and hydraulic pressure source.

10. The apparatus of claim 1, wherein said loader further comprises:

a meter for measuring the normal load.

11. The apparatus of claim 1, wherein said shearer is a load press, an air piston, a hydraulic actuator or a loading rod having weights coupled thereto.

12. The apparatus of claim 1, wherein said shearer further comprises:

a meter for measuring the force.

13. The apparatus of claim 1, further comprising:

a detector for measuring normal deformation of the first and second geoengineering materials.

14. The apparatus of claim 1, further comprising:

a meter for measuring linear displacement at the interfaces.

15. The apparatus of claim 1, further comprising:

containment members for coupling a geomaterial to the outer load plates.

16. The apparatus of claim 1, further comprising:

a tank for immersing the inner and outer assemblies in a liquid.

* * * * *